United States Patent [19]

Anderson et al.

[11] Patent Number: 4,513,294

[45] Date of Patent: Apr. 23, 1985

[54] PHYSIOLOGICAL TREND DATA RECORDER

[75] Inventors: Donald G. Anderson, Meriden, Conn.; Elisa M. Ferrara-Jordan, Longmeadow, Mass.

[73] Assignee: American Home Products Corporation, New York, N.Y.

[21] Appl. No.: 398,019

[22] Filed: Jul. 14, 1982

[51] Int. Cl.³ .......................... G01D 9/00; A61B 5/04
[52] U.S. Cl. .............................. 346/33 ME; 346/1.1; 128/710; 128/900
[58] Field of Search ............... 346/33 ME, 1.1; 128/702–704, 710, 900

[56] References Cited

U.S. PATENT DOCUMENTS

| | | | |
|---|---|---|---|
| 3,650,263 | 3/1972 | Kowalski et al. | 346/33 ME UX |
| 3,799,148 | 3/1974 | Rowen | 128/704 |
| 3,958,563 | 5/1976 | Fernandez et al. | 346/33 ME X |
| 4,051,522 | 9/1977 | Healy et al. | 346/33 ME X |
| 4,090,505 | 5/1978 | Mortara | 346/33 ME X |
| 4,369,496 | 1/1983 | Parsons et al. | 346/33 ME X |
| 4,422,081 | 12/1983 | Woods | 346/33 ME |

*Primary Examiner*—George H. Miller, Jr.
*Attorney, Agent, or Firm*—Edward M. Blocker

[57] ABSTRACT

A strip chart recorder and method for recording trend signals representative of a physiological condition on a strip chart responsive to the occurrence of an alarm condition. Trend signals representative of said physiological condition in the past are stored. Upon the occurrence of the alarm condition, the stored trend signals are recorded at a faster than real time rate.

2 Claims, 20 Drawing Figures

FIG.1

BACKGROUND PROGRAM

INITIALIZATION ROUTINE (MODE=1)

STORE ROUTINE (MODE=2)

FIG. 7A

- START
- 179: PERFORM STUFF $ QUEUE
- 216: a $ DATA = HOLD $ a $ DATA
- 218: b $ DATA = HOLD $ b $ DATA
- 220: MOTOR $ DRIVE = ZERO
- 222: ALARM $ SIGNAL = TRUE?
  - NO → I
  - YES → 224: PEN $ HEAT = MAXIMUM → H

FIG. 7B

- H
- 226: aw $ COUNTER = 2000
- 228: INTER $ ALARM $ GAP = TRUE?
  - NO → 230: GAP $ COUNTER = ZERO
  - YES → 232: GAP $ COUNTER = 300
- 234: SET MODE = 3
- I
- 224: PERFORM CHECK $ INPUTS
- RETURN

WAIT ROUTINE (MODE = 3)

PHYSIOLOGICAL TREND DATA RECORDER

BACKGROUND

The present invention relates to the automatic recording of physiological trend signals on a strip chart.

In hospital intensive care practice, the patients' vital signs are monitored continuously for the prompt detection of life threatening conditions. Existing monitoring instruments automatically detect a serious degradation in vital signs to give prompt alarm signals when such a condition occurs. When such a condition exists, it is necessary for the medical professional to diagnose the patient's condition promptly in order to take remedial action. The availability of a continuous trend record of the degraded vital sign for the time period immediately preceding the alarm event is important for a rapid and accurate diagnosis.

SUMMARY

In accordance with one aspect of the present invention, there is provided a strip chart recorder responsive to the occurrence of an alarm condition for recording trend signals representative of a physiological condition on a strip chart. The recorder comprises means for recording the trend signals on the strip chart at a rate selectable in response to a rate signal. Means are provided for storing trend signals representative of said physiological condition in the past. Additional means are provided for controlling the storing means to provide the stored trend signals to the recording means responsive to the occurrence of an alarm condition and for providing a rate signal to the recording means selected to control the recording means to record the stored trend signals at a faster than real time rate.

In accordance with a preferred embodiment of the present invention, the controlling means is operative upon completion of recording of the stored trend signals to provide trend signals representative of the physiological condition at points in time subsequent to those represented by the stored trend signals to the recording means and to provide a rate signal to the recording means selected to control the recording means to record the subsequent trend signals at a real time rate.

In accordance with a further aspect of the present invention, a method of recording trend signals representative of a physiological condition on a strip chart responsive to the occurrence of an alarm condition is provided. The method comprises the steps of: storing trend signals representative of said physiological condition in the past; and responding to the occurrence of the alarm condition to record the stored trend signals at a faster than real time rate.

In accordance with a preferred embodiment of the present invention, the method comprises the further step of, upon completion of recording of the stored trend signals, recording at a real time rate trend signals representative of the physiological condition at points in time subsequent to those represented by the stored trend signals.

By recording the stored data at a faster than real time rate, the present invention makes a trend record of the prealarm condition data available to the medical professional very shortly after the alarm condition occurs, thus facilitating a rapid and accurate diagnosis of the patient's condition.

BRIEF DESCRIPTION OF THE DRAWINGS

The present invention, as well as further objects and features thereof, will be understood more clearly and fully from the following description of certain preferred embodiments when read with reference to the companying drawings, in which.

DETAILED DESCRIPTION OF A PREFERRED EMBODIMENT

Figure 1:
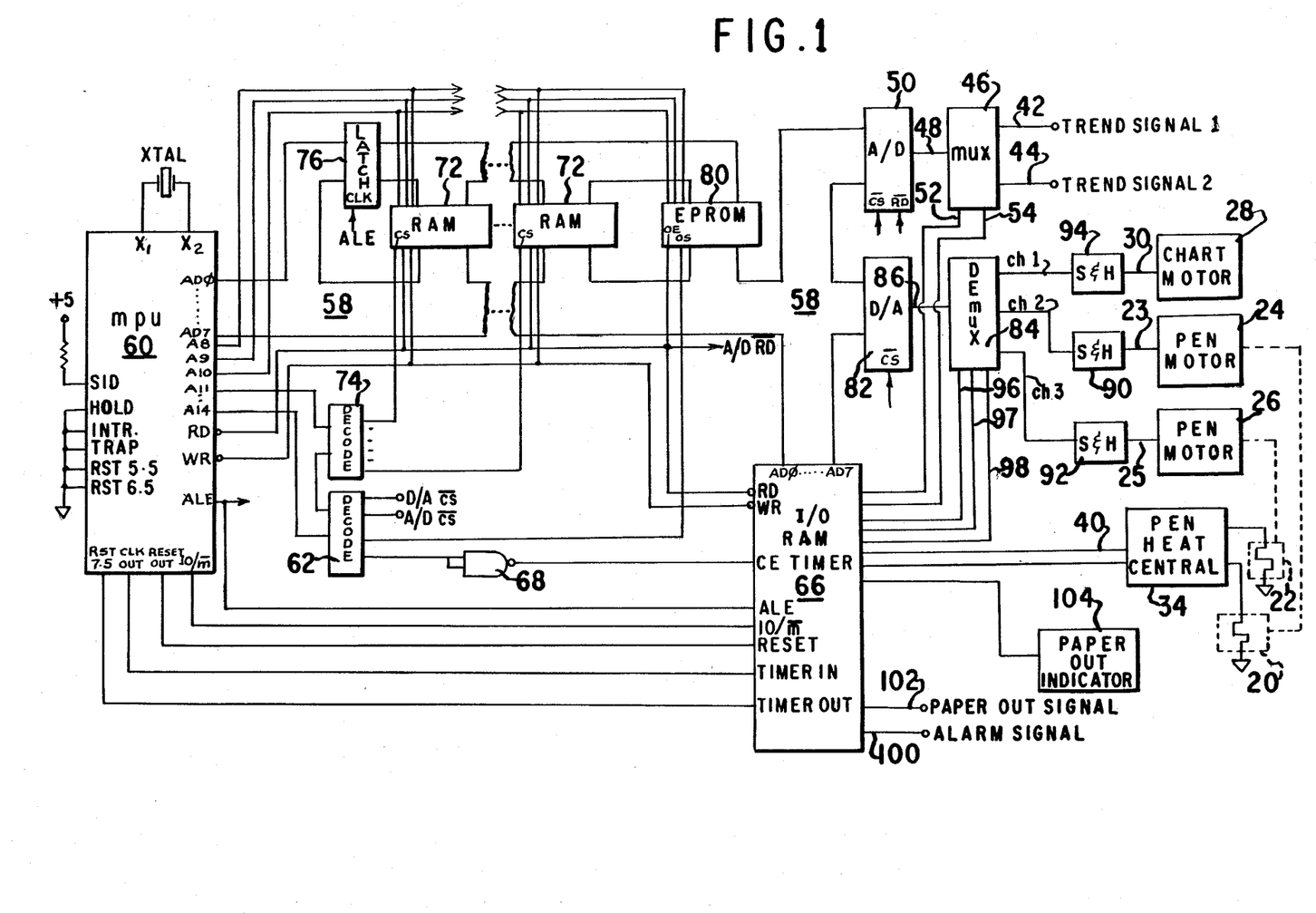
FIG. 1 is a block diagram illustrating a strip chart recorder in accordance with the present invention.

The strip chart recorder of FIG. 1 includes a first thermal recording pen 20 and a second thermal recording pen 22 provided for simultaneously recording on a thermally sensitive strip chart two respective trend signals representative of physiological conditions of a patient being monitored. The position of pen 20 with respect to the strip chart scale is controlled by a pen motor 24, while the position of pen 22 with respect to the strip chart scale is controlled by a pen motor 26. Each of pen motors 24 and 26 are controlled in turn by a firmware programmed, microprocessor based control unit (described in greater detail below) through the provision of an a$data signal to a control terminal 23 of motor 24 and the provision of a b$data signal control terminal 25 of motor 26.

The strip chart is driven past the pens 20 and 22 by a chart motor 28 having a speed selectable according to a signal received at a chart motor input 30 of the chart motor 28. The control unit also serves to provide a motor$drive signal to the chart motor input 30 in order to control the rate at which the strip chart is driven past the recording pens 20 and 22.

The thermal recording pens 20 and 22 operate to create a record upon thermally sensitive chart paper by raising the temperature thereof to a predetermined level at desired locations on the chart. Accordingly, it is necessary to control the temperature of the pens in accordance with the selected chart speed so that the trend record produced by the pens is sufficiently dark yet not unduly broad. Accordingly, a pen heat control 34 is provided for this purpose and has two output terminals each coupled to a respective one of recording pens 20 and 22 to provide a heating current thereto under the control of the control unit to vary the temperature of the pens 20 and 22 in accordance with the speed of the strip chart. The operation of pen heat control 34 for this purpose is determined by the control unit through the provision of a pen$heat signal to an input bus 40 of pen heat control 34.

The strip chart recorder is provided with two trend signal input terminals 42 and 44 for receiving respective trend signals 1 and 2. Trend signals 1 and 2 may be, for example, heart rate and respiration rate signals provided by a vital signs monitor, as well as other types of physiological signals, such as blood pressure, ECG, etc. The recorder has an input multiplexer (Mux) 46 having two inputs, each coupled to a respective one of input terminals 42 and 44, and a single output 48. The output 48 is connected to the input of an analog-to-digital converter (A/D converter) 50. Multiplexer 46 is operative to couple either its input terminal 42 or its input terminal 44 to its output 48 to couple the selected one of terminals 42 and 44 to the input terminal of A/D converter 50 in response to respective multiplexing control signals received at control terminals 52 and 54 of multiplexer 46. The multiplexing control signals are provided by the control unit in a manner described hereinbelow. A/D converter 50 is operative upon the receipt of chip select ($\overline{CS}$) and read ($\overline{RD}$) signals to convert the analog signal provided at terminal 48 to an 8-bit binary level signal at its output which is coupled to the multiplexed address-/data bus 58 of a microprocessor unit 60.

In the strip chart recorder illustrated in FIG. 1, the microprocessor unit 60 is a type 8085A manufactured by Intel Corporation. The $\overline{RD}$ input of A/D converter 50 is coupled with the $\overline{RD}$ output terminal of the microprocessor unit 60 and the $\overline{CS}$ input of A/D converter 50 is coupled with a first output terminal of a first address decoder 62, having an input coupled with the higher order address bus of the microprocessor unit 60. The $\overline{CS}$ and $\overline{RD}$ signals are provided by the microprocessor unit 60 under the control of firmware programs described hereinbelow to A/D converter 50 to effect the analog to digital conversion of the selected analog input trend signal. The multiplexing control signals provided to terminals 52 and 54 of multiplexer 46 are provided under the control of the unit 60 by a port of a I/O, RAM, TIMER unit 66 programmed as an output port by the unit 60. Unit 66 in the embodiment of FIG. 1 is a model 8156 unit manufactured by Intel Corporation. The address/data bus 58 of the unit 60 has its AD0 through AD7 terminals connected respectively to the corresponding terminals of the unit 66, while the RD, WR, ALE, IO/$\overline{M}$ terminals of the unit 60 are connected to the corresponding terminals of the unit 66. The Reset Out, CLK Out and RST 7.5 terminals of the unit 60 are connected respectively to the RESET, Timer In and Timer Out terminals of the unit 66. A second output terminal of decoder 62 is coupled through an inverter 68 to the chip enable (CE) terminal of the unit 66 through which it is addressed by the unit 60. The Hold, INTR, Trap, RST 5.5 and RST 6.5 terminals of the unit 60 are coupled to ground. The SID terminal of the unit 60 is coupled through a resistor to a +5 voltage reference, while a 6.144 MHz crystal is connected to the $X_1$ and $X_2$ terminals of the unit 60.

The strip chart recorder has a 16K memory which provides waveform storage for trend signals 1 and 2 in separate 8K recirculating memory queues implemented under firmware control. The 16K memory comprises eight 2K-word by 8-bit RAM's 72, of which only two are shown for simplicity. The individual RAM's 72 are selected by the unit 60 by a higher order address provided by terminals A11–A14 of the unit 60 which are decoded by a second decoder 74 which is operable to provide individual select signals to the CS terminals of the individual RAM's 72. Lower level addresses to the RAM's 72 are provided from the terminals AD0–AD7, A8, A9 and A10 of the unit 60. The multiplexed address signals from the AD0–AD7 are provided to the RAM's 72 through a latch 76 which is clocked by the ALE signal from the unit 60. Read and write commands to the RAM's 72 are provided from the RD and WR terminals of the unit 60.

The firmware program is stored in an electrically programmable read only memory (EPROM) 80 which is selected by the unit 60 through the provision of an address to decoder 62 which outputs a select signal on a third output terminal to the output select (OS) terminal of the EPROM 80. The lower order addresses to the EPROM 80 are provided in the same manner as those provided to the RAM's 72. The RD terminal of the unit 60 is coupled to the output enable (OE) terminal of the EPROM 80.

The digitized trend signals 1 and 2 provided by the A/D converter 50 are stored in memory respectively as the a$data and b$data signals. The a$data and b$data signals are converted to analog signals for recording on the strip chart by means of a digital-to-analog converter (D/A converter) 82 and demultiplexed by a demultiplexer (Demux) 84 which receives the multiplexed analog signals from an output 86 of D/A converter 82, providing the converted a$data signal to an output channel (Ch) 2 and the b$data signal to an output channel (Ch) 3. Each of channels 2 and 3 is coupled to the input terminals of respective sample and hold circuits 90 and 92 which provide the a$data and b$data signals in continuous analog form respectively to the terminals 23 and 25 for controlling the positions of the pens 20 and 22 for recording the trend signals 1 and 2 on the strip chart. The motor$drive signal to the chart motor 28 is provided in the same fashion through D/A converter 82 and demultiplexer 84 to an output channel (Ch) 1 to a third sample and hold circuit 94 thus to provide the motor$drive signal in continuous analaog form to the chart motor 28 to control the rate at which the strip chart record is driven. The D/A converter 82 is selected by the unit 60 through a higher level address provided through its terminals A11–A14 which is decoded by decoder 62 and provided on a fourth output terminal thereof coupled with the $\overline{CS}$ terminal of the D/A converter 82. The selection of the desired output channel from the demultiplexer 84 is controlled through the provision of demultiplexing control signals to channel select terminals 96, 97 and 98 of demultiplexer 84, the control signals being provided via the programmed output port of the unit 66 under the control of unit 60.

The strip chart recorder of FIG. 1 is also provided with a third input terminal 100 and a fourth input terminal 102, each coupled to respective terminals of a port of the unit 66 programmed by the unit 60 as an input port. Input terminal 100 is provided to receive an alarm signal from a monitoring instrument indicating that a patient's condition has worsened, thus to signal to the strip chart recorder that stored trend signals should be rapidly recorded at a faster than real time rate to provide such information quickly to the medical professional for diagnosis of the patient's condition. The strip chart recorder samples the terminal 100 through the unit 66 periodically to detect the receipt of such an alarm signal, as will be explained in greater detail below.

The input terminal 102 is provided to receive a paper out signal which indicates that the recorder's supply of strip chart paper has been exhausted. The state of terminal 102 is periodically tested by the strip chart recorder to determine whether this has occurred, so that the recorder may stop the chart motor 28 and the pen motors 24 and 26, turn off the heating current to the pens 20 and 22 and provide an output signal through the programmed output port of the unit 66 to a paper out indicator 104 to signal the need for additional chart paper.

Figure 6:
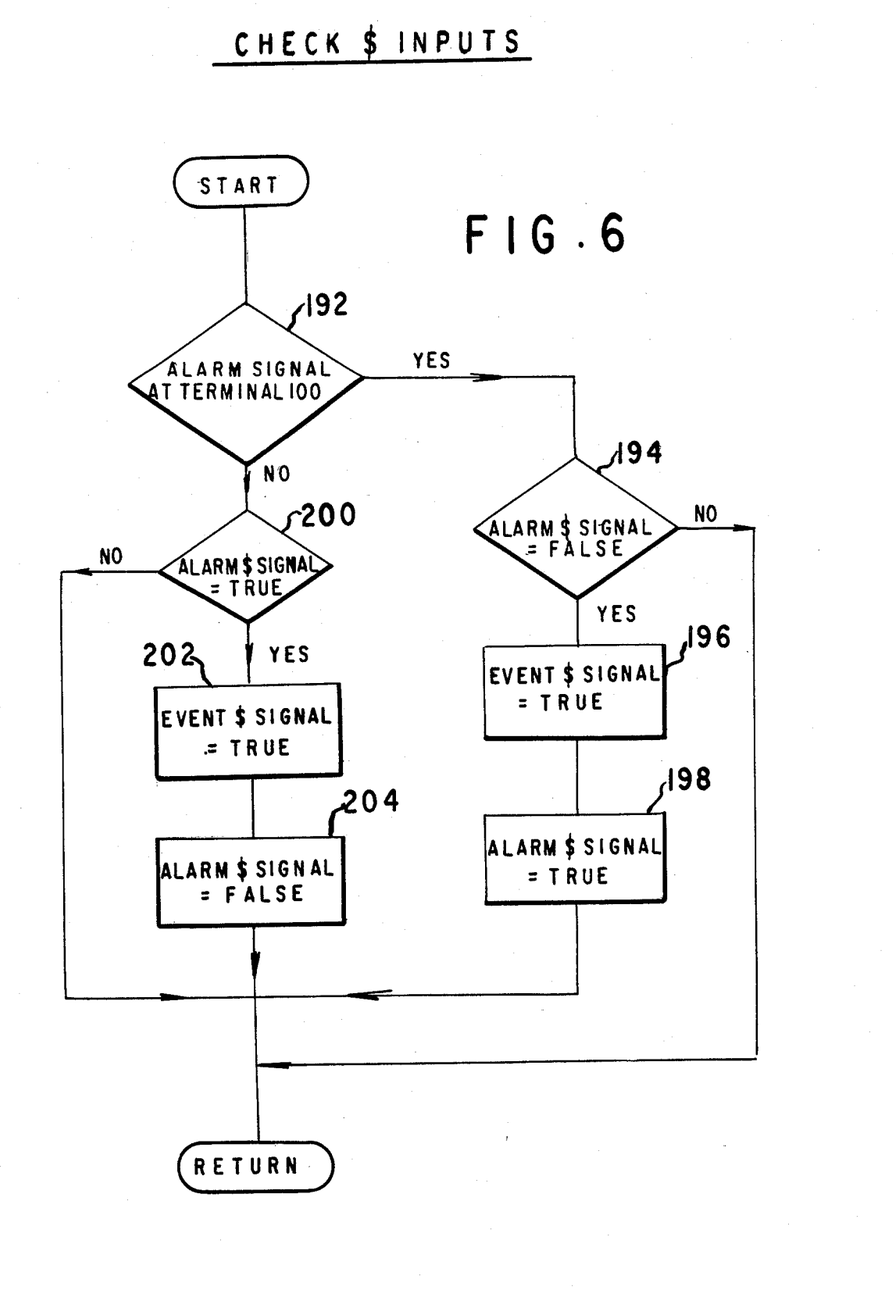
FIG. 6 is a flow chart of a Check$Inputs utility routine which is called by other routines for use, inter alia, in detecting the receipt of an alarm signal by the strip chart recorder of FIG. 1.

The operation of the strip chart recorder of FIG. 1 will now be explained in greater detail with reference to the remaining figures illustrating the sequence of operations embodied in the firmware program permanently stored in the EPROM 80 for controlling the operation of the recorder. Briefly, after initialization of the system by the Background program illustrated in FIGS. 2A and 2B, the Interrupt 7.5 program illustrated in FIGS. 3A and 3B is called upon the receipt of a clock pulse by the Rst 7.5 input terminal of the unit 60 from the Timer Out terminal of the unit 66. The clock pulses are generated by the unit 66 which divides the clock signal from the CLK Out terminal of the unit 60 to produce a 480 Hz clock signal at the Timer Out terminal of the unit 66. Accordingly, the Interrupt 7.5 program is called 480 times each second. The Interrupt 7.5 program itself controls the input and output of data by the system, except for the input of the alarm signal which is accomplished by the Check$Inputs utility routine illustrated in FIG. 6. The Interrupt 7.5 program also calls various routines illustrated in the succeeding figures for processing the data received and generated by the microprocessor unit under program control, and enables interrupts so that Interrupt 7.5 will be called each time a clock signal is received at Rst 7.5 of the unit 60.

Figure 2A:
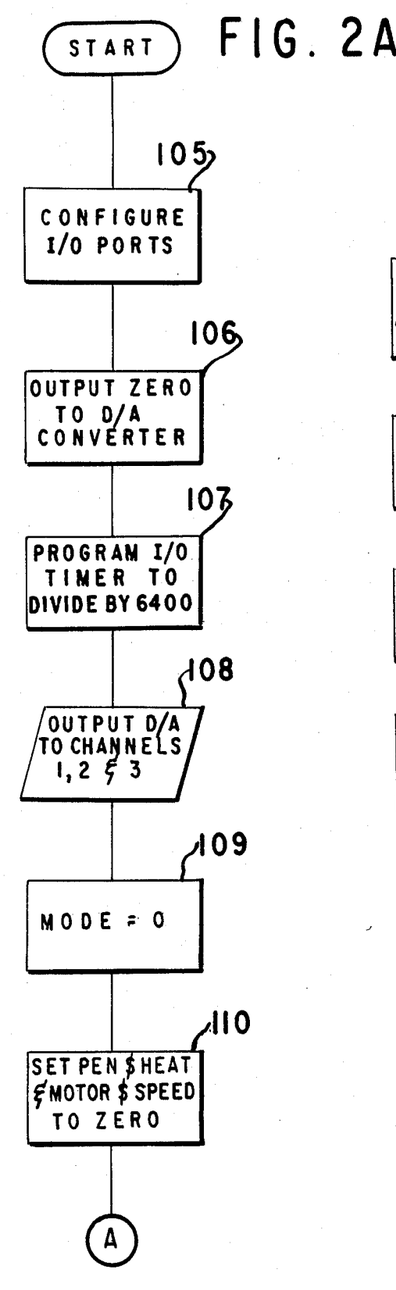
FIGS. 2A and 2B are flow charts of a Background program for use in controlling the operation of the strip chart recorder of FIG. 1.
Figure 2B:
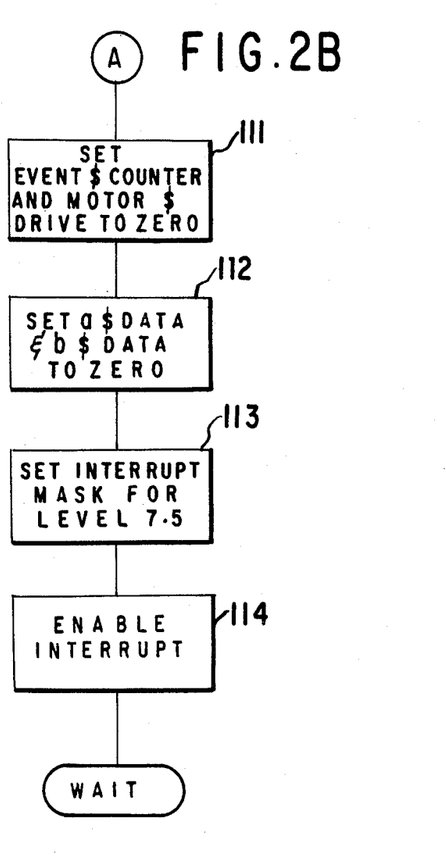
Figure 3A:
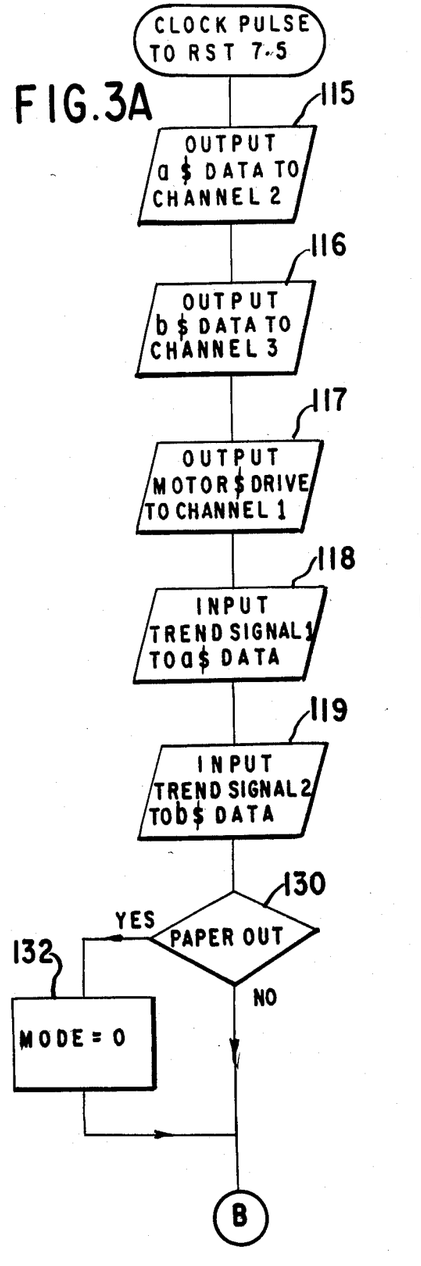
FIGS. 3A and 3B are flow charts of an Interrupt 7.5 program which coordinates the operation of the strip chart recorder of FIG. 1 upon completion of the Background program of FIGS. 2A and 2B, by calling lower level routines illustrated in the following figures.
Figure 3B:
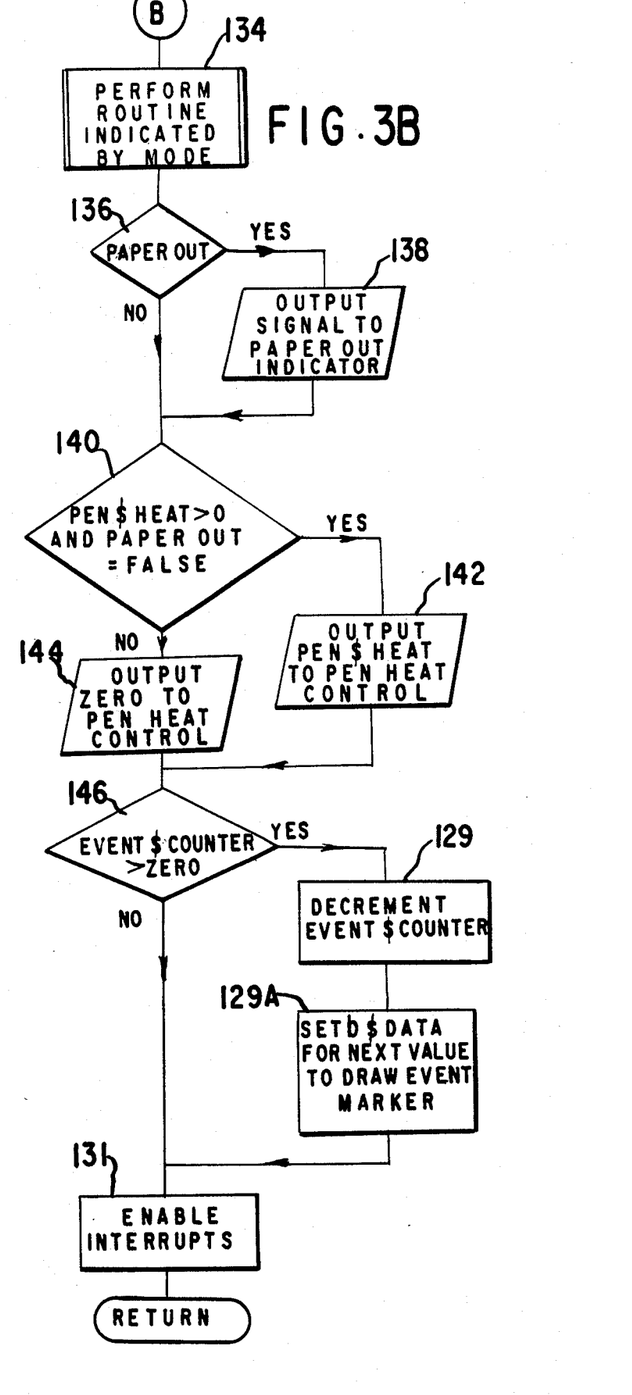
Figure 4:
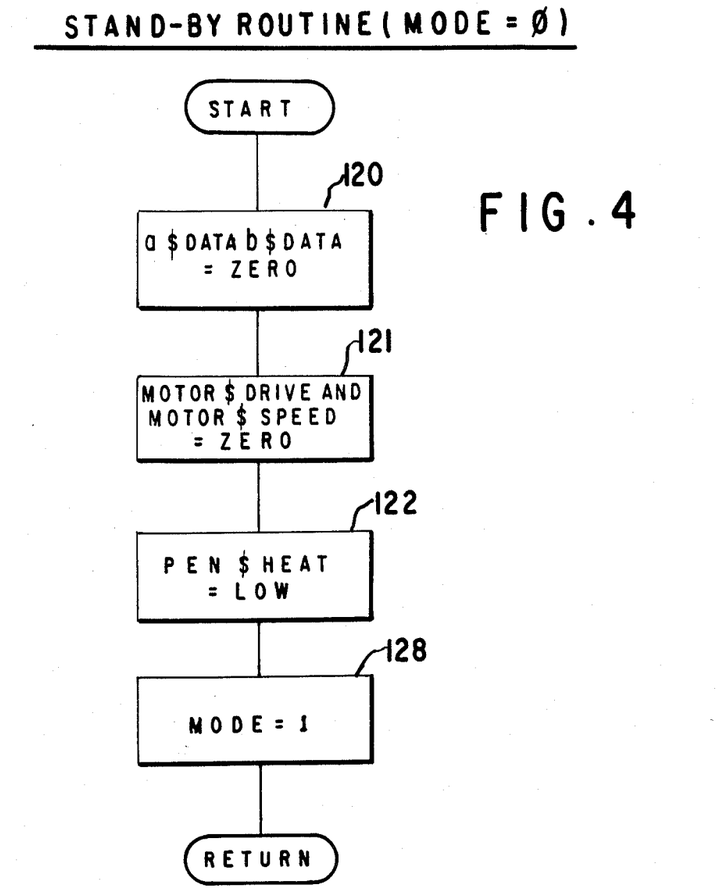
FIG. 4 is a flow chart of a Stand-by routine (mode=0) which is called by the Interrupt 7.5 program upon the occurrence of certain conditions.

With reference to FIGS. 2A and 2B, the Background program there illustrated is called first when power is applied to the recorder in order to program the ports of the unit 66 (statement 105 of FIG. 2A), to program the timer of the unit 66 to produce the 480 Hz clock signal (statement 107), to set the signal levels on the output channels 1, 2 and 3 to 0 (statements 106 and 108), to set the mode equal to 0 (so that the Interrupt 7.5 program will first call the Stand-by routine illustrated in FIG. 4 when processing the first interrupt clock pulse; see statement 109), as well as to initialize certain data structures (statements 110, 111 and 112) and enable interrupts (statements 113 and 114) so that the Interrupt 7.5 program will be called upon receipt of the next clock pulse at Rst 7.5 of the unit 60.

When the Interrupt 7.5 program (FIGS. 3A and 3B) is called upon the next clock pulse, the motor$drive, a$data and b$data signals (set at 0 by the Background program) are output by the D/A converter 82 and the demultiplexer 84, respectively, to channels 1, 2 and 3 for provision to the chart motor 28, and the pen motors 24 and 26 (statements 115, 116 and 117). Accordingly, the chart motor is initially off and the pens are maintained in their respective 0 positions on the strip chart scales. Then the trend signal 1 and trend signal 2 are input and stored in a$data and b$data (statements 118 and 119). With reference to statements 130 and 132, the signal at input terminal 102 is tested to determine whether the strip chart paper has been exhausted, in which case the mode of operation is set to Stand-by. Accordingly, statement 134 would then call the Stand-by routine (FIG. 4) which sets various data structures to disable the recording of information. In particular, when Interrupt 7.5 is again called, statements 115–117 will output zero level signals to the pen motors 24 and 26 and the chart motor 28 by virtue of statements 120 and 121 of the Stand-by routine. Statements 136 and 138 of Interrupt 7.5 again test input terminal 102 to determine whether the paper out indicator 104 should be activated. Statements 140, 142 and 144 control the provision of the pen$heat signal to the pen heat control 34 for selecting an appropriate heating current to the pens 20 and 22. Statements 140 and 144 ensure that the pens will not be heated if either the Paper Out signal on terminal 102 is false (indicating that the paper has been exhausted) or the pen$heat signal equals 0. If statement 134 had called the Stand-by routine, statement 122 thereof would have set pen$heat to low, a value which signals the control 34 to heat the pens 20 and 22 insufficiently to mark the strip chart paper but reduces the response (heating) time of the pens in the event of a mode change calling for the recording of information. Statements 146, 129 and 129A are explained below in connection with the explanation of the Dump$Queue routine, FIG. 11. Statement 131 enables the processing of interrupts, which were disabled automatically by the unit 60 after receipt of the previous clock pulse at RST 7.5.

Figure 5A:
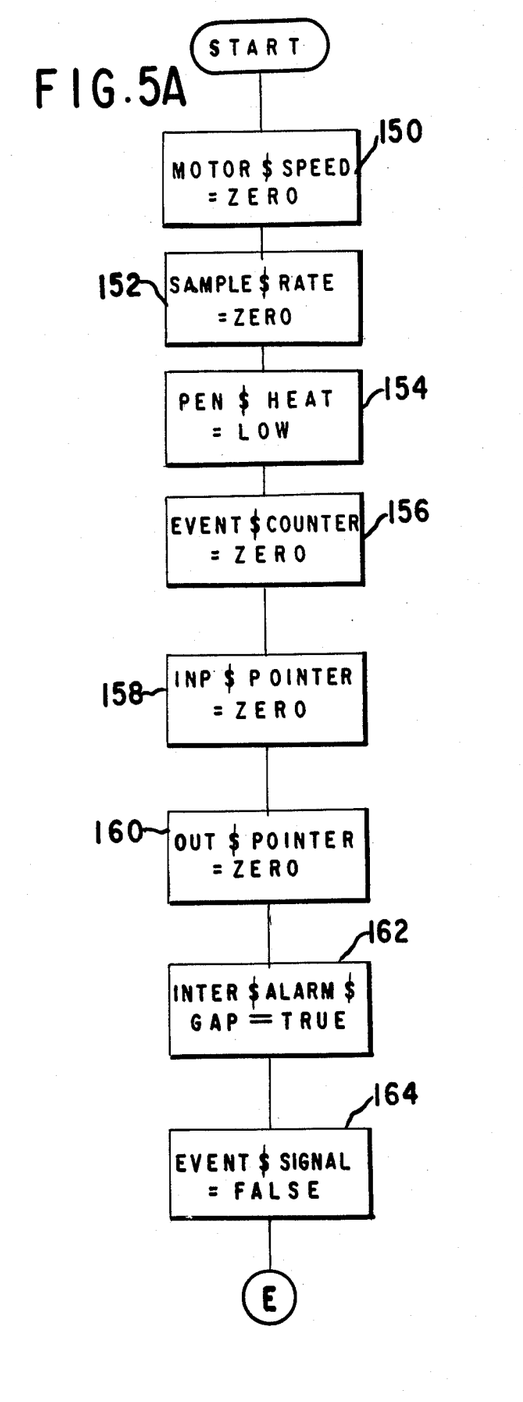
FIGS. 5A and 5B are flow charts of an Initialization routine (mode=1) called by the Interrupt 7.5 program to establish initial values for necessary data structures.
Figure 5B:
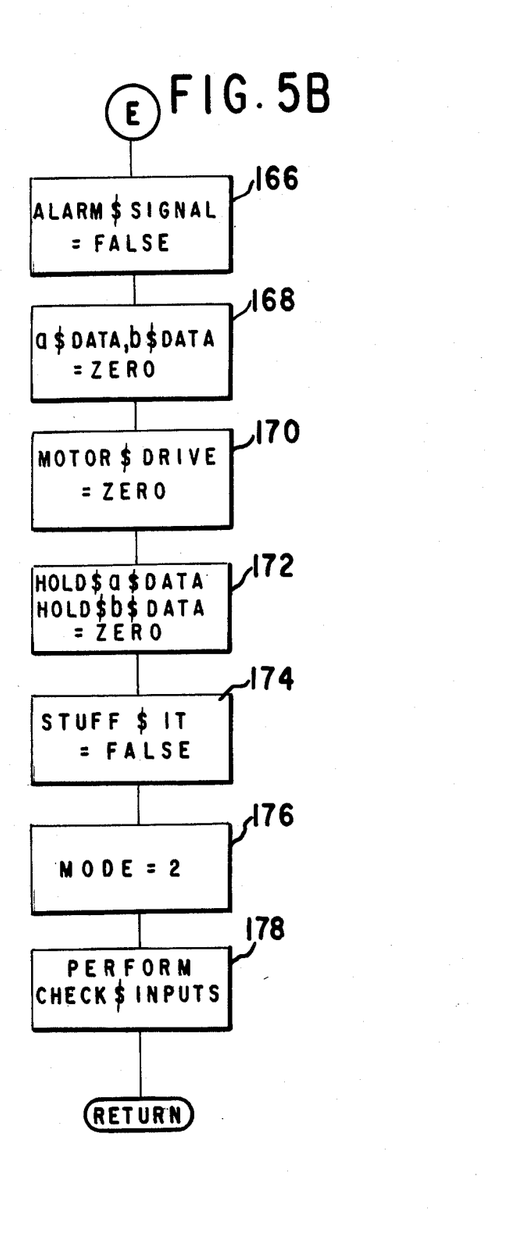
Figures 7A, 7B:
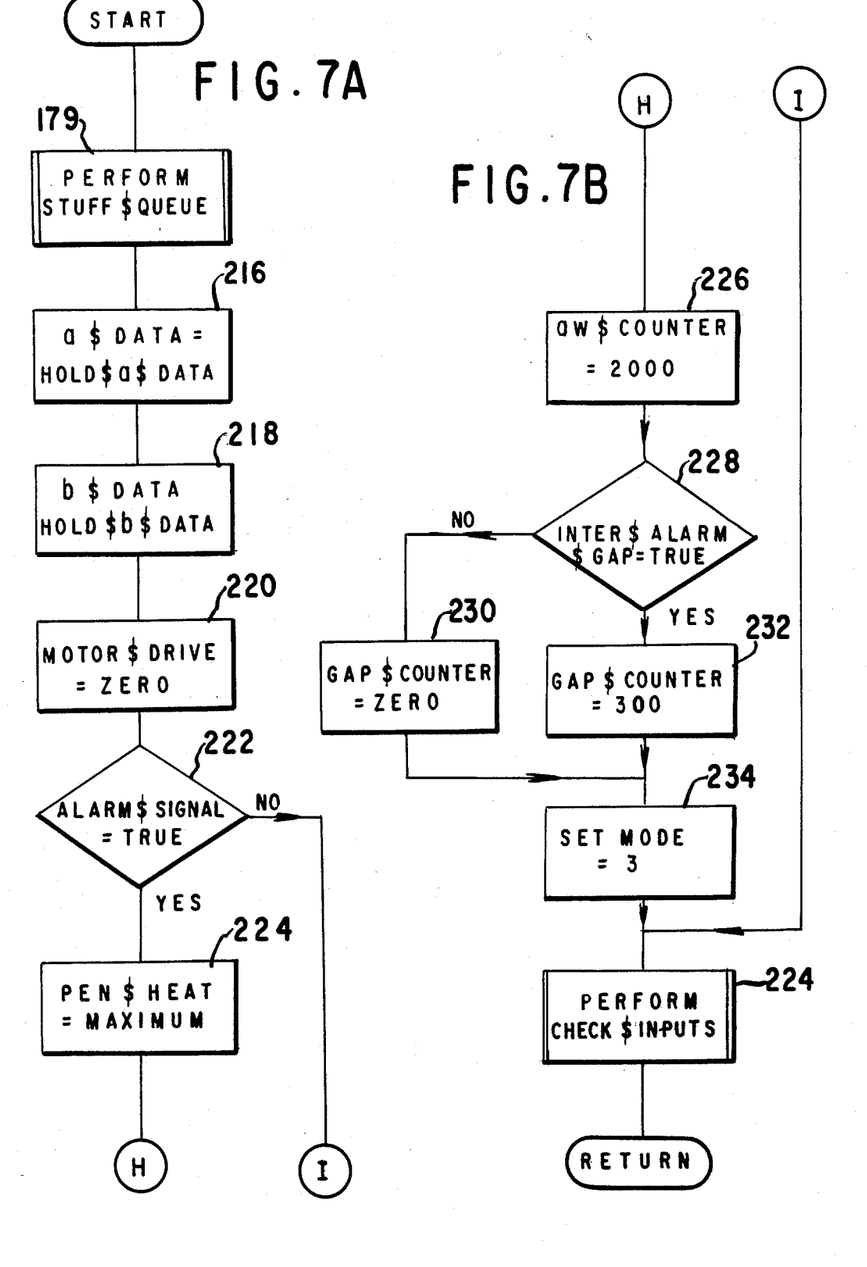
FIGS. 7A and 7B are flow charts of a Store routine (mode=2) called by the Interrupt 7.5 program.

After the first interrupt, the mode has been reset to 1 by statement 128 of the Stand-by routine. Accordingly, upon the second interrupt, if the paper has not been exhausted (so that the Stand-by routine has once again been called pursuant to statements 130 through 134), the initialization routine illustrated in FIGS. 5A and 5B is called by statement 134 in the Interrupt 7.5 program. Statements 150 through 174 initialize various data structures for the proper operation of the recorder in subsequent modes of operation. Statement 176 sets the mode to 2 so that the Store routine illustrated in FIGS. 7A and 7B will be called by the Interrupt 7.5 program upon receipt of the next interrupt clock pulse at RST 7.5 if the paper has not been exhausted. Statement 178 calls the utility routine Check$Inputs which basically checks the input terminal 100 for receipt of an alarm signal and sets the necessary data structures accordingly. The Check$Inputs utility routine will be discussed in greater detail in connection with the Store routine illustrated in FIGS. 7A and 7B.

Upon the following interrupt, the mode having been reset to 2, the Interrupt 7.5 program will call the Store routine after outputing existing data values and inputing trend signal data to a$data and b$data (statements 115 through 119), assuming that the paper has not been exhausted. The Store routine commences by calling the utility routine Stuff$Queue illustrated in FIGS. 8A and 8B. Briefly, the Stuff$Queue routine serves to store selected values of a$data and b$data in the recorder's main memory in time sequential locations. In order to permit subsequent recording of the stored data at a faster than real time rate in response to the receipt of an alarm signal (in the present embodiment, at a rate 8 times faster than a real time rate) a 3-bit counter, sample$rate, is incremented by 1 each time the Stuff$Queue routine is called (statement 180). With reference to statement 182, the current values of a$data and b$data are stored only when sample$rate has been reset to 000, i.e., only once every 8 times that Stuff$Queue is called (except when a real time recording rate is desired, in which case a value, stuff$it, has been set as true, as described below). The actual storage of a$data and b$data in their respective recirculating queues, designated a$queue and b$queue, takes place pursuant to statements 184 and 186. It should be noted that each time the data is stored in a$queue and b$queue, the variable inp$pointer is incremented by 1 (see statement 190) so that time sequential signals are stored in sequentially addressed locations in memory. When the variable inp$pointer reaches 8K, it is reset to 0, so that the queues once again recirculate. Refer to statements 192 and 194.

With reference once again to statements 186 and 188, the value event$signal is stored in b$queue whenever event$signal is true (i.e., equal to 11111111B), while statement 188 ensures that event$signal will be reset once a true event signal has been stored. At this point refer once again to the Check$Inputs utility routine illustrated in FIG. 6 which sets the variable event$signal upon the detection of an alarm signal at input terminal 100. Assuming that an alarm signal has been received, statement 192 will direct the program to statement 194 which checks to ensure that the presence of an alarm signal has not already been detected and stored in the data structure alarm$signal, so that event$signal will be true only once for each alarm. Assuming that an alarm signal had not previously been detected, the program will proceed to statements 196 and 198 in sequence to set event$signal and alarm$signal both true. It should be noted that the next time Check$Inputs is called, alarm$signal will be true so that statements 196 and 198 will be bypassed and event$signal will not once again be set to true after it has been reset to false by statement 188 of Stuff$Queue. In the event that the alarm signal at the input port resets after alarm$signal has been set, statement 200 together with statement 204 ensures that alarm$signal will be reset after event$signal has been set (statement 202).

The variable out$pointer serves to indicate that point in the queues from which data is to be obtained for recording. Set to 0 in the initialization routine, FIG. 5A, out$pointer will not equal inp$pointer until the queues have been filled (inp$pointer having been incremented in statement 190). Accordingly, statement 206 in FIG. 8B will not be answered afirmatively until the queues have been filled at least once, whereupon out$pointer will be incremented in accordance with statement 208. The next time that Stuff$Queue is called, inp$pointer will be incremented once again per statement 190 and statement 206 will once again be affirmative so that out$pointer will once again be incremented. Statements 210 and 212 reset out$pointer to 0 when it reaches 8K. Accordingly, out$pointer will always be greater than inp$pointer by 1 at the end of Stuff$Queue so long as the queues are full and out$pointer will then point to the oldest data in the queues. When statement 206 indicates that the queues are full, a flag inter$alarm$gap is set to true (statement 214) which indicates that a gap should be inserted between any previously recorded trend signals and any trend signals to be recorded in the future, since upon the next interrupt, the oldest data in the queues will be discarded and, thus, there will be a discontinuity between the previously recorded trend signals and any trend signals to be recorded in the future.

Figure 9A:
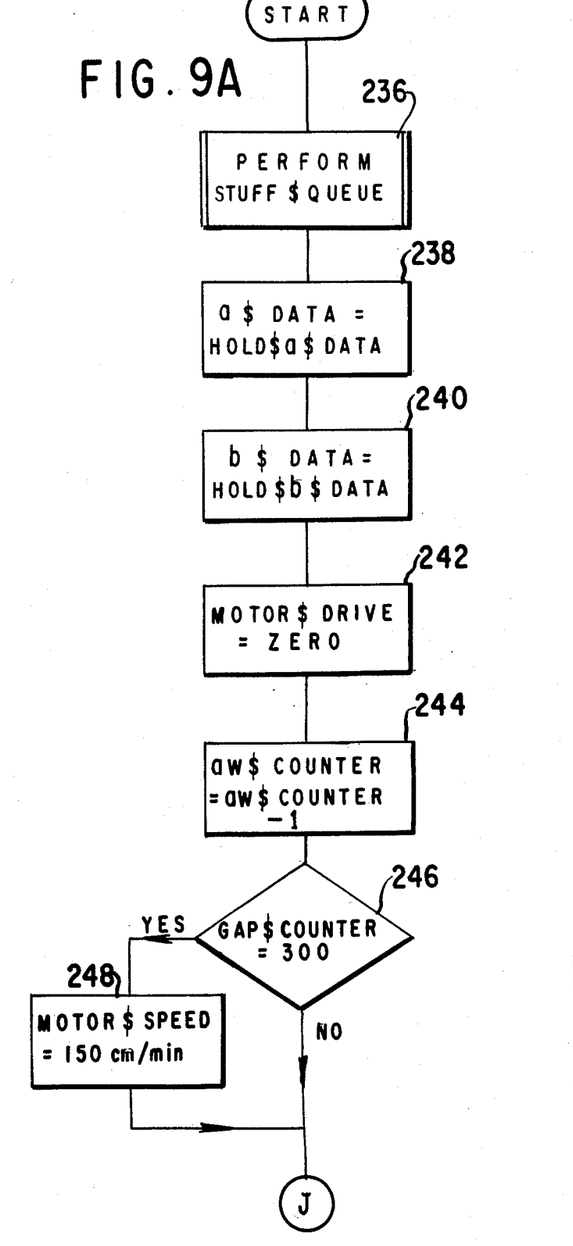
FIGS. 9A and 9B are flow charts of a Wait routine (mode=3) called by the Interrupt 7.5 program in response to the receipt of an alarm signal and serving to initialize necessary data structures preparatory to faster than real time recording of stored trend signals.
Figure 9B:
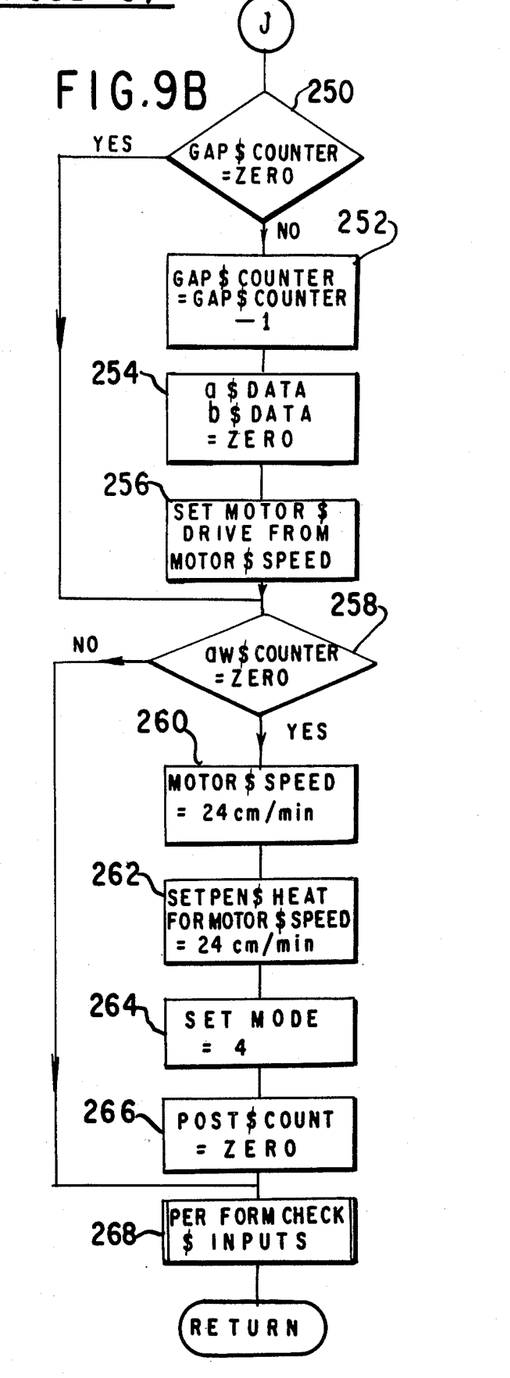
Figures 10A, 10B:
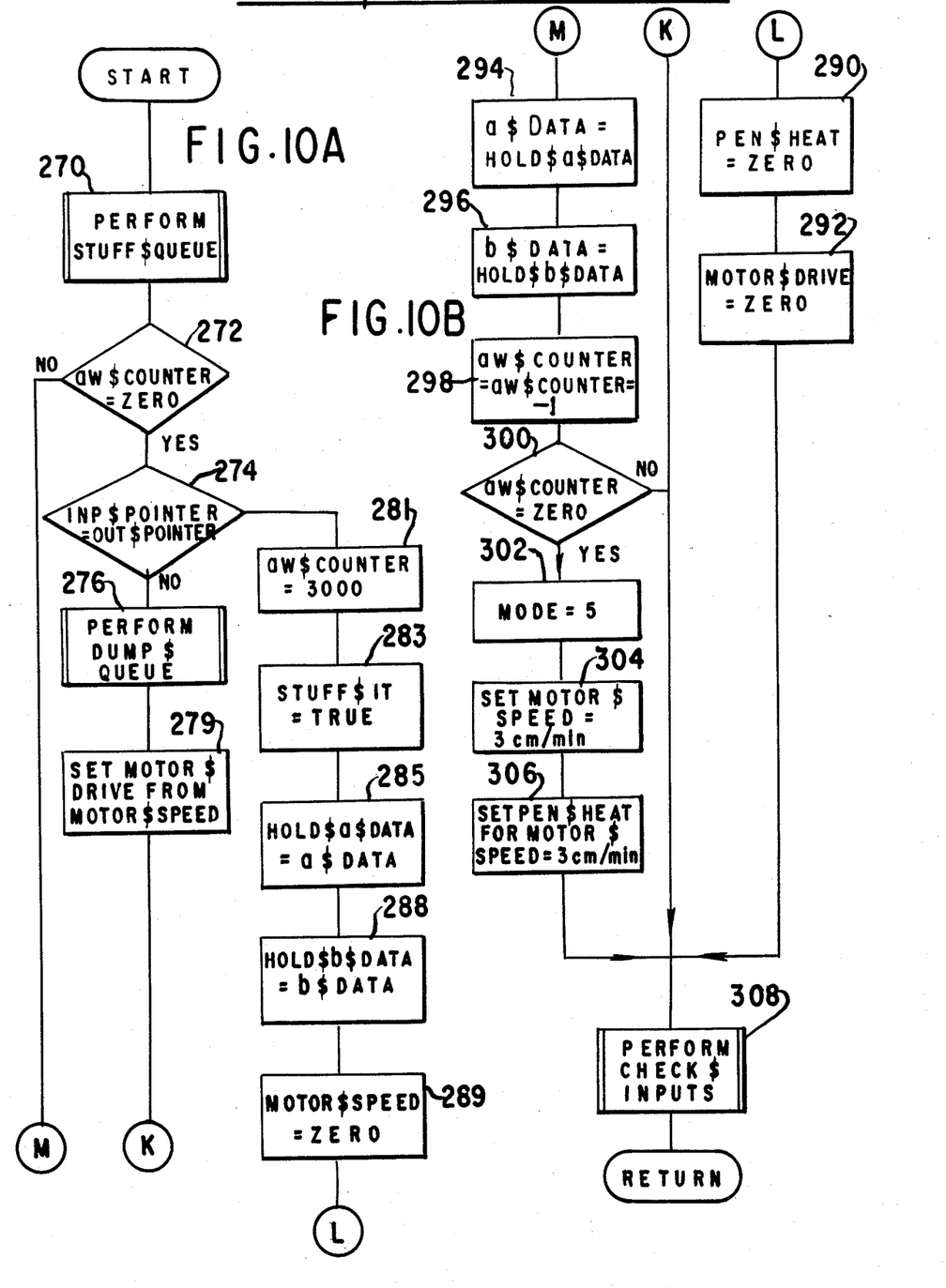
FIGS. 10A and 10B are flow charts of a Catch$Up routine (mode=4) called by the Interrupt 7.5 program upon completion of necessary initializations and serving to control faster than real time recording of stored trend signals.

Upon completion of Stuff$Queue, the Store routine continues by performing three operations, indicated by statements 216, 218 and 220, which serve to hold the pens 20 and 22 stable and prevent the chart motor 28 from running so long as the Store routine is being performed. The step indicated by statement 222 tests the value of alarm$signal to determine whether an alarm signal has been received at terminal 100. If this is not the case, the Store routine continues by performing the step indicated by statement 224 to call the Check$Inputs utility routine so that, if an alarm signal has been received at terminal 100, this condition may be detected. Accordingly, in the absence of the receipt of an alarm signal at terminal 100, the Interrupt 7.5 program will continue to call the Store routine to continuously store the most recent trend signals. If, however, performance of the Check$Inputs routine results in the detection of an alarm signal for the first time, both alarm$signal and event$signal will be true (statements 192, 194, 196 and 198). In this event, the Store routine will proceed from the operation indicated by statement 222 to that indicated by statement 224 which sets the pen$heat signal to a maximum level so that pens 20 and 22 can be rapidly heated to an appropriate level for recording at a rate of 24 centimeters per second. Then, in accordance with statement 226, a counter denominated aw$counter is set to a value selected for controlling the amount of time for heating pens 20 and 22 at the maximum level to reach an appropriate temperature for recording on the strip chart which will be driven at a rate of 24 centimeters per second. Statements 228, 230 and 232 test inter$alarm$gap to determine whether, if trend signals previously had been recorded, the queues have been filled completely with new trend signal data and, accordingly, a gap between the old and new data should be inserted. It will be seen below that the flag inter$alarm$gap is reset to false after the completion of recording of previous data, so that until the queues are once again filled with data, and inter$alarm$gap is set to true by the Stuff$Queue routine, no gap will be inserted between the previously recorded data and stored data to be recorded on the strip chart. The operations indicated by the statements 230 and 232 serve to set a counter designated gap$counter which serves in the Wait routine, FIGS. 9A and 9B, to determine whether a gap should be inserted in the recorded data and, if so, how wide that gap should be. Upon completion of the operation indicated either by statement 230 or 232 the Store routine continues by setting the mode to 3, i.e., to perform the Wait routine when Interrupt 7.5 is called upon receipt of the next interrupt clock pulse (statement 234).

The Wait routine inserts a delay in the recording of information after the detection of an alarm signal to permit the pens to heat up sufficiently for recording at the faster than real time rate of 24 centimeters per minute, to provide for a gap in the strip chart record if that is called for by the value of gap$counter, and to perform necessary initializations for the recording of data pursuant to the Catch$Up routine. With reference to statement 236 of the Wait routine, the recorder continues to store trend signals in the queues by calling the Stuff$Queue routine. With reference to statements 238 and 240, the pens 20 and 22 are held stable so long as the Wait routine is being performed each time Interrupt 7.5 is called (i.e., mode remains equal to 3). Statement 242 ensures that, so long as no gap is being inserted in the recorded trend records, the chart motor 28 remains off so long as the mode remains equal to 3. As indicated by statement 244, each time the Wait routine is called by Interrupt 7.5, the aw$counter will be decremented by 1 thus to provides a means for timing the duration that the pens 20 and 22 are being heated at a maximum value to reach an appropriate temperature for 24 centimeter per minute recording.

With reference now to statements 246 through 256, upon the initial performance of the Wait routine, when the gap$counter equals 300, the motor speed is set to a relatively high value of 150 centimeters per minute for creating the gap as quickly as possible. Accordingly, upon the next interrupt, motor$drive will be output to chart motor 28 which will run thereafter at 150 cm/min. continuously until the gap counter has reached 0 (i.e., in approximately six-tenths of a second since the Interrupt 7.5 routine is called approximately once every 2 milliseconds). Meanwhile, the pens will be held stable (statement 254). It should be noted that, where a gap is to be produced, this occurs during the first six-tenths of a second during which the mode is equal to 3 so that the pens have not heated up sufficiently to mark the paper when the chart motor is turned on to produce the gap. With reference to statements 258 through 266, once the aw$counter has reached 0 through repeated decrementing in accordance with statement 244, the pens have reached sufficient temperature for recording at 24 centimeters per minute and, as indicated by statements 260, 262 and 264, the values motor$speed and pen$heat are set for 24 centimeters per minute recording and the mode is set to 4 from 3 so that upon the next interrupt, the Catch$Up routine will be called to rapidly record the already stored trend signal data. In accordance with statement 266, a value post$count is set to 0 as an initialization in preparation for real time recording, as described below. With reference to statement 268, the recorder once again tests for the receipt of an alarm signal by performing Check$Inputs.

Upon the following interrupt, Interrupt 7.5 calls the Catch$Up routine (mode=4). With reference to statement 270, the recorder continues to store trend signal data in the recirculating queues during the Catch$Up routine. Since aw$counter equaled 0 at the end of the Wait routine, when Catch$Up is first performed, the operation indicated by statement 274 follows immediately from that indicated by statement 272. When the Catch$Up routine is first performed, inp$pointer will not be equal to out$pointer so that the the Catch$Up routine then performs Dump$Queue.

Figure 11:
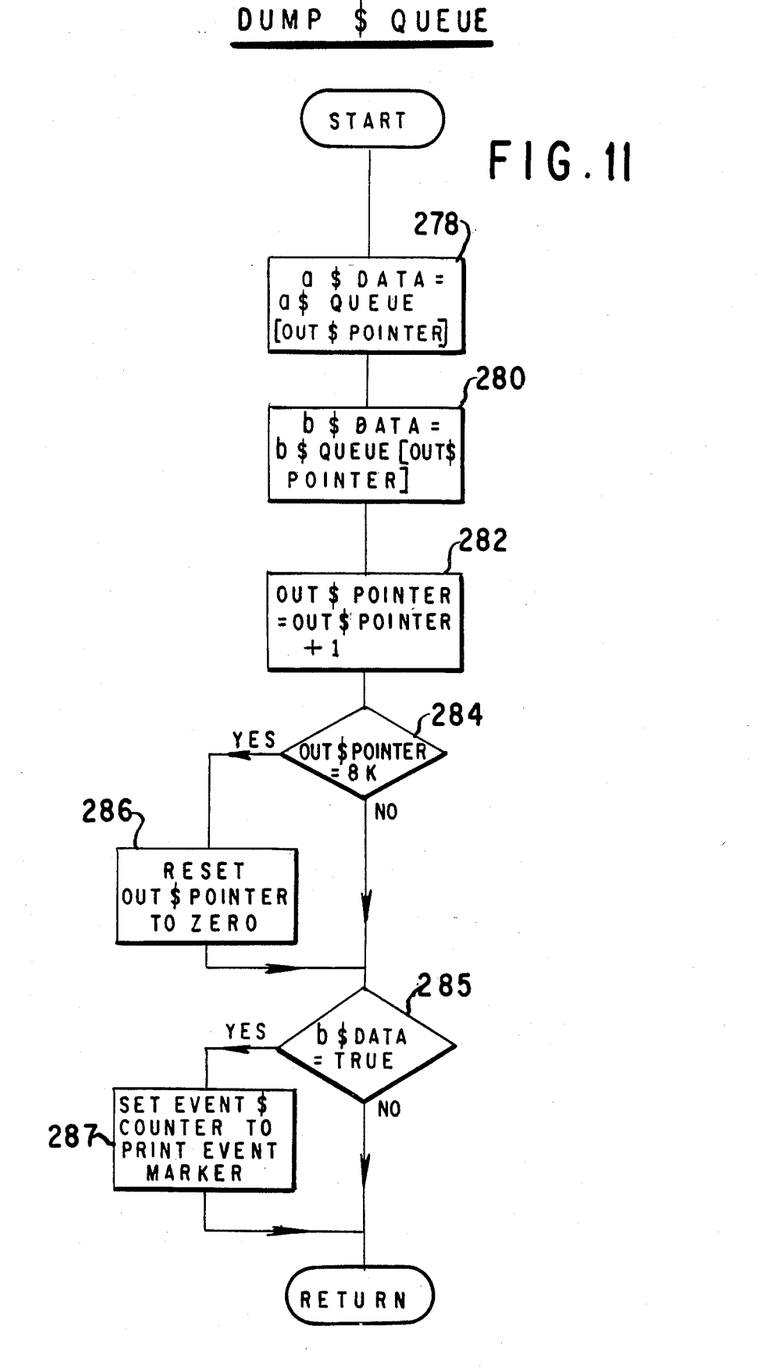
FIG. 11 is a flow chart of a Dump$Queue utility routine called by other routines for accessing data from the recirculating memory.

With reference to FIG. 11, the Dump$Queue routine, as indicated by statements 278 and 280, loads the contents of the respective queues addressed by out$pointer in a$data and b$data so that upon the performance of Interrupt 7.5 the pen motors 24 and 26 will operate to position the pens 20 and 22 for recording the stored values of the trend signals retrieved from the queues during the immediately preceding Interrupt 7.5 program. The operations indicated by statements 285 and 287 serve to set the counter denominated event$counter whenever b$data is true, indicating the time at which an alarm signal was detected by the Check$Inputs routine and stored in b$queue by virtue of the operation represented by statement 186 in Stuff$Queue. The value of event$counter serves to determine the width of an event marker produced on the strip chart by pen 22 which makes a sequence of marks equal in number to the value of event$counter. The individual marks are made by virtue of the operations represented by statements 146 and 129A of Interrupt 7.5, while event$counter is decremented by 1 every interrupt (statement 129) as each mark is made.

Figure 8A:
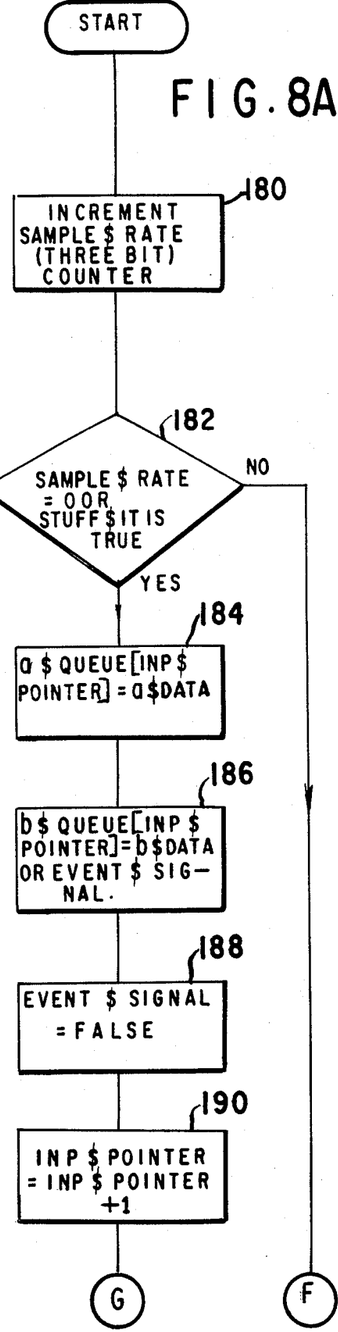
FIGS. 8A and 8B are flow charts of a Stuff$Queue utility routine which is called by other routines when trend signals are to be stored in recirculating memory.
Figure 8B:
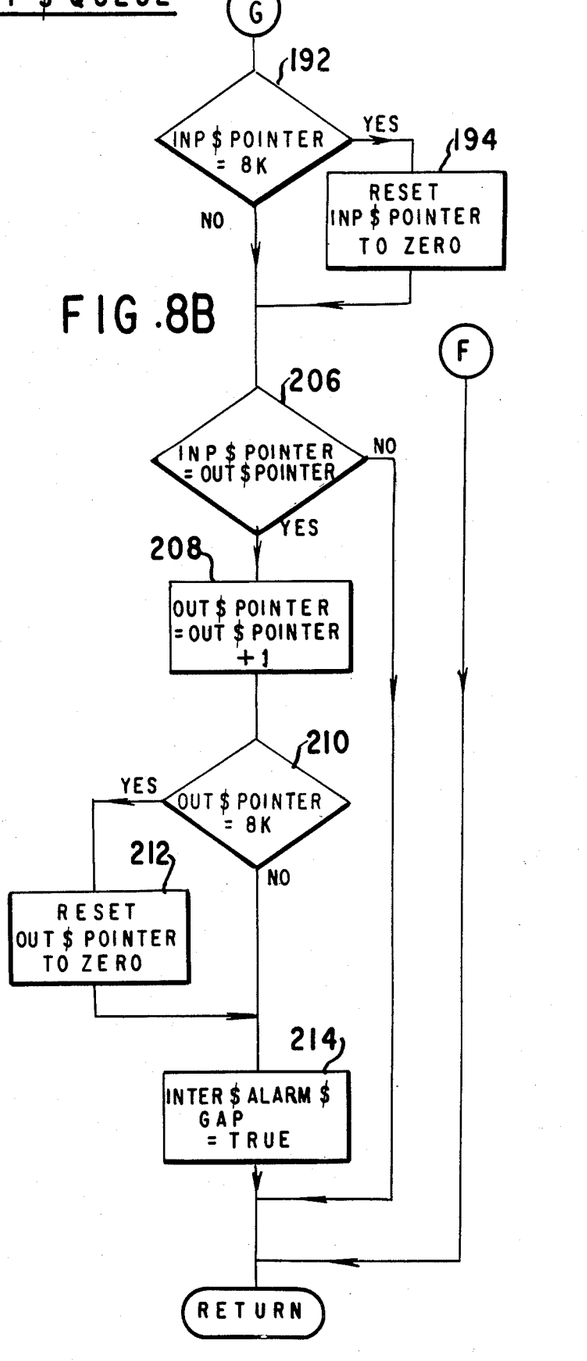

With reference to statements 282, 284 and 286, each time Dump$Queue is performed, i.e., once each clock period so long as mode equals 4, the out$pointer is incremented by 1 and, when out$pointer reaches 8K, it is reset to 0. With reference to FIG. 8A, statements 182 and 190, it will be seen that inp$pointer is incremented only once every 8 clock cycles, since stuff$it is still false. Accordingly, through repeated performance of the Catch$Up routine upon each new clock cycle, the contents of the queues will be recorded at a rate 8 times faster than trend signals are being recorded in the queues, so that eventually the data being recorded will correspond to that received during the previous clock cycle, whereupon out$pointer will have "caught up" to inp$pointer, indicating that all previously stored data has been recorded. As indicated by statement 279, the motor$drive signal for driving the chart motor 28 is set from motor$speed, previously set to 24 centimeters per minute.

When all of the data previously stored in the queues has been recorded, inp$pointer will equal out$pointer and the Catch$Up routine will proceed from statement 274 to perform the operations indicated by statements 281, 283, 285 and 288 through 292 to intialize a cool down period for the pens 20 and 22. The duration of this period is determined by aw$counter which is stored with an appropriate value, per statement 281 and, in accordance with statement 290, pen$heat is set to 0 to cool down the pens as fast as possible. Statements 285, 288, 289 and 292 serve to prevent the recording of data until the pens have been cooled sufficiently for real time recording at a rate of 3 centimeters per minute. As indicated by statement 283, stuff$it is set to true so that each time Stuff$Queue is performed subsequently, trend signal data will be stored every clock cycle for real time recording. After the operations indicated by statements 281, 283, 285 and 288 through 292 have been performed once, the following performance of the Catch$Up routine after the next interrupt will result in the performance of the operations indicated by statements 294, 296 and 298 after the operation indicated by statement 272. These operations serve to hold the pens stable as they cool down and to decrement the aw$counter by 1 each clock cycle. With reference to statement 300, when aw$counter has reached 0, the mode is changed to 5 and the motor$speed and pen$heat signals are reset for 3 centimeters per minute recording (refer to statements 302, 304 and 306). With reference to statement 308, as in the case of the previous modes, the routine Check$Inputs is performed once each clock cycle so long as the mode is equal to 4.

Figure 12A:
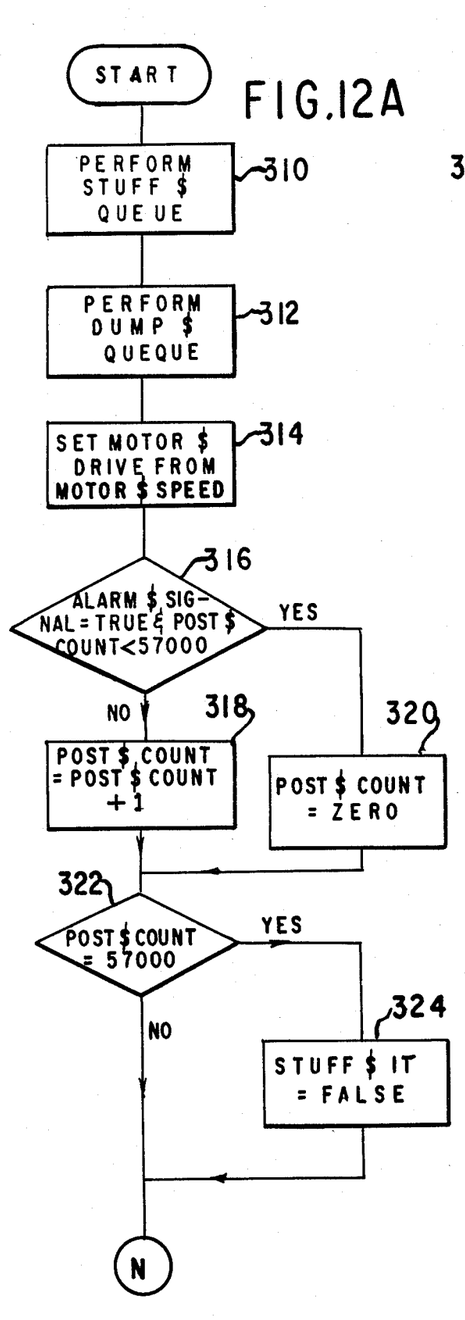
FIGS. 12A and 12B are flow charts of a Real$Time routine (mode=5) called by the Interrupt 7.5 program for controlling the real time rate of trend signal recording following the completion of the Catch$Up routine.
Figure 12B:
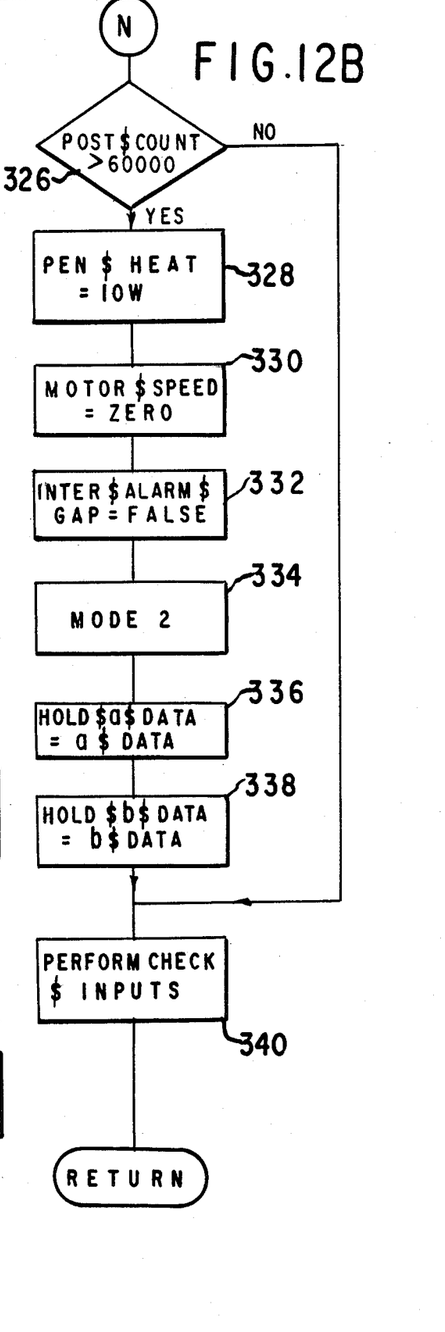

Upon the next interrupt, Interrupt 7.5 calls the Real$-Time routine (FIGS. 12A and 12B). It should be noted initially that through the duration of the cool down period provided for in the Catch$Up routine, Stuff$Queue has been performed (see statement 270) but not Dump$Queue. Accordingly, when the mode is set to 5 initially, a certain amount of trend signal data has been stored in the queues and has not yet been recorded on the strip chart. The Real$Time routine serves for recording the stored data at a real time rate for a first predetermined period of time until all of the stored data has been recorded or unless an alarm signal is detected before the expiration of a second predetermined period of time slightly less than the first predetermined period. Upon completion of the Real$Time routine, the mode is reset to 2 to recommence the storing of trend signal data while the recorder waits for the receipt of a new alarm signal.

With reference to statements 310 and 312 of the Real$Time routine, current trend signal data is stored in the queues and stored trend signal data is read from the queues upon each clock cycle (stuff$it being true). However, the data read from the queues will be older than that being stored in the queues during the respective clock cycle by a period of time equal to the pen cool down period. With reference to statement 314, motor$drive is set from motor$speed, previously set at 3 centimeters per minute at the end of the Catch$Up routine. The operations indicated by statements 316, 318 and 320 collectively serve to increment the counter post$count (set to 0 during the Wait routine) or, in the event that an alarm signal has been detected and post$count is less that 57,000, post$count is reset to 0 to provide for the continued recording of trend signal data representative of points in time subsequent to the second alarm event indicated by the receipt of an alarm signal at terminal 100. When post$count reaches 57,000, stuff$it is reset to false (see statements 322 and 324) to provide for the storing of data in only 1 out of every 8 counts while data is read from the queues and recorded upon each clock cycle to provide for the complete recording of all stored data which occurs when post$count exceeds 60,000. When post$count exceeds 60,000 (refer to statements 326 through 338) the mode is reset to 2, a$data and b$data are held constant to prevent the pens 20 and 22 from moving, motor$speed is set to 0 in order to turn off the chart motor 28, pen$heat is set to low so that the pens cease marking the strip chart and inter$alarm$gap is set to false, so that there will be no gap inserted upon the recording of new data until the queues are filled (refer to statement 179 in FIG. 7A and statement 214 in FIG. 8B). As in the performance of the routines indicated by modes 1 through 4, at the completion of the Real$Time routine, Check$Inputs is once again performed in order to detect the presence of an alarm signal at terminal 100 (see statement 340).

Accordingly, it will be seen that the strip chart recorder herein disclosed provides the capability of storing the most recently acquired trend signal data representing a plurality of physiological functions for a selected period of time as well as the capability of rapidly providing a strip chart record of such stored data at a faster than real time rate (in the case of the particular recorder disclosed herein, at a rate 8 times faster than the data was received for storing) upon the occurrence of an alarm condition. The disclosed strip chart recorder also provides the capability of recording trend signal data representative of such physiological conditions at points in time subsequent to those represented by the stored trend data signals upon the completion of the recording of the stored signals. Accordingly, the strip chart recorder of the present invention is capable upon the occurrence of an alarm condition of very rapidly providing pre-alarm condition physiological data to the medical professional who must quickly diagnose the patient's condition, while the strip chart recorder continues to provide the data at a real time rate after the stored data is recorded. The strip chart recorder of the present invention also provides such data in an easy to read and economical format.

The advantages of the present invention, as well as certain changes and modifications of the disclosed embodiments thereof, will be readily apparent to those skilled in the art. It is the applicants' intention to cover by their claims all those changes and modifications which can be made to the embodiment of the invention herein chosen for the purpsoes of the disclosure without departing from the spirit and scope of the invention.

We claim:

1. A strip chart recorder responsive to the occurrence of an alarm condition for recording first and second trend signals representative of a physiological condition on a strip chart comprising:

recording means operable for recording the first trend signals on the strip chart at a faster than real time rate in response to a first rate signal and for recording the second trend signals on the strip chart at a real time rate in response to a second rate signal;

storing means for storing said first trend signals representative of said physiological condition in the past; and controlling means operable for controlling the storing means so as to provide the stored first trend signals to the recording means in response to the occurrence of the alarm condition and for providing the first rate signal, the second rate signal and the second trend signals to the recorder; said second trend signals representative of the physiological condition at points in time subsequent to those represented by the first rate signal and being provided to the recorder after recordation of the first trend signals.

2. A method of recording first and second trend signals representative of a physiological condition on a strip chart which is responsive to the occurrence of an alarm condition comprising the steps of:

storing the first trend signals representative of said physiological condition in the past;

responding to the occurrence of the alarm condition to record the stored first trend signals at a faster than real time rate; and thereafter recording at a real time rate the second trend signals representative of the physiological condition at points in time subsequent to those represented by the stored first trend signals.

* * * * *